United States Patent [19]

Guo et al.

[11] Patent Number: 5,554,186
[45] Date of Patent: Sep. 10, 1996

[54] BILEAFLET MECHANICAL HEART VALVE HAVING CROPPED SLOT PIVOT CONFIGURATION AND METHOD FOR PREVENTING BLOOD STAGNATION THEREIN

[75] Inventors: George X. Guo, Dove Canyon; Robert Stobie, Mission Viejo, both of Calif.

[73] Assignee: Baxter International Inc., Deerfield, Ill.

[21] Appl. No.: 362,633

[22] Filed: Dec. 22, 1994

[51] Int. Cl.⁶ ........................................................ A61F 2/24
[52] U.S. Cl. ................................................................ 623/2
[58] Field of Search ........................... 623/2, 900, 66

[56] References Cited

U.S. PATENT DOCUMENTS

| | | | |
|---|---|---|---|
| 4,178,639 | 12/1979 | Bokros | 3/1.5 |
| 4,254,508 | 3/1981 | Bokros | 623/2 |
| 4,272,854 | 6/1981 | Bokros | 623/2 |
| 4,276,658 | 7/1981 | Hanson et al. | 3/1.5 |
| 4,308,624 | 1/1982 | Klawatter | 623/2 |
| 4,328,592 | 5/1982 | Klawitter | 623/2 |
| 4,363,142 | 12/1982 | Meyer | 623/2 |
| 4,373,216 | 2/1983 | Klawitter | 3/1.5 |
| 4,443,892 | 4/1984 | Klawitter | 623/2 |
| 4,443,894 | 4/1984 | Klawitter | 3/1.5 |
| 4,446,577 | 5/1984 | Meyer et al. | 3/1.5 |
| 4,451,937 | 6/1984 | Klawitter | 623/2 |
| 4,605,408 | 8/1986 | Carpentier | 623/2 |
| 4,676,789 | 6/1987 | Sorensen et al. | 623/2 |
| 4,692,165 | 9/1987 | Bokros | 623/2 |
| 4,822,353 | 4/1989 | Bokros | 623/2 |
| 4,863,458 | 9/1989 | Bokros | 623/2 |
| 4,863,459 | 9/1989 | Olin | 623/2 |
| 4,872,875 | 10/1989 | Hwang | 623/2 |
| 4,888,010 | 12/1989 | Bokros | 623/2 |
| 4,892,540 | 1/1990 | Vallana | 623/2 |
| 4,923,465 | 5/1990 | Knoch et al. | 623/2 |
| 4,935,030 | 6/1990 | Alonso | 623/2 |
| 4,995,881 | 2/1991 | Knoch et al. | 623/2 |
| 5,002,567 | 3/1991 | Bona et al. | 623/2 |
| 5,061,278 | 10/1991 | Bicer | 623/2 |
| 5,078,738 | 1/1992 | Coueil | 623/2 |
| 5,108,425 | 4/1992 | Hwang | 623/2 |
| 5,116,366 | 5/1992 | Hwang | 623/2 |
| 5,116,367 | 5/1992 | Hwang et al. | 623/2 |
| 5,123,920 | 9/1990 | Bokros | 623/2 |

(List continued on next page.)

FOREIGN PATENT DOCUMENTS

| | | |
|---|---|---|
| 0050439A2 | 4/1982 | European Pat. Off. . |
| 0091746B1 | 6/1986 | European Pat. Off. . |
| 211576A | 2/1987 | European Pat. Off. . |
| 0465383A1 | 6/1991 | European Pat. Off. . |
| 0541215A1 | 8/1992 | European Pat. Off. . |
| 0515324A1 | 11/1992 | European Pat. Off. . |
| 2018396A | 10/1979 | United Kingdom . |
| 2055452A | 3/1981 | United Kingdom . |
| WO86/05383 | 9/1986 | WIPO . |
| WO91/11973 | 8/1991 | WIPO . |
| WO9202197 | 2/1992 | WIPO . |
| WO9221305 | 12/1992 | WIPO . |
| WO9301767 | 2/1993 | WIPO . |

Primary Examiner—David H. Willse
Assistant Examiner—Bruce E. Snow
Attorney, Agent, or Firm—Stetina, Brunda & Buyan; Raymond Sun

[57] ABSTRACT

A bileaflet mechanical cardiovascular valve comprising an annular valve body having a pair of occluder leaflets pivotally mounted therewithin. The occluder leaflets are pivotally mounted within the valve body by the snap-fitting of ear member which extend from the top and bottom ends of the occluder leaflets into corresponding cropped pivot slots formed within the annular valve body. Each cropped pivot slot comprises a spheroidal depression or recess having a first flat cropped edge and a second flat cropped edge. The ear members of the occluder leaflets are sized and configured relative to the cropped pivot slots to facilitate opening and closing of the occluder leaflets with minimal likelihood of hemolysis or thrombotic complications. Additionally disclosed is a specialized machine tool and method for machining the cropped pivot slots in the annular valve body.

26 Claims, 3 Drawing Sheets

U.S. PATENT DOCUMENTS

| | | | |
|---|---|---|---|
| 5,137,532 | 8/1992 | Bokros et al. | 623/2 |
| 5,147,390 | 9/1992 | Campbell | 623/2 |
| 5,152,785 | 10/1992 | Bokros et al. | 623/2 |
| 5,171,263 | 12/1992 | Boyer et al. | 623/2 |
| 5,178,632 | 4/1993 | Hanson | 623/2 |
| 5,192,309 | 3/1993 | Stupka et al. | 623/2 |
| 5,192,313 | 3/1993 | Budd et al. | 623/2 |
| 5,197,980 | 3/1993 | Gorshkov et al. | 623/2 |

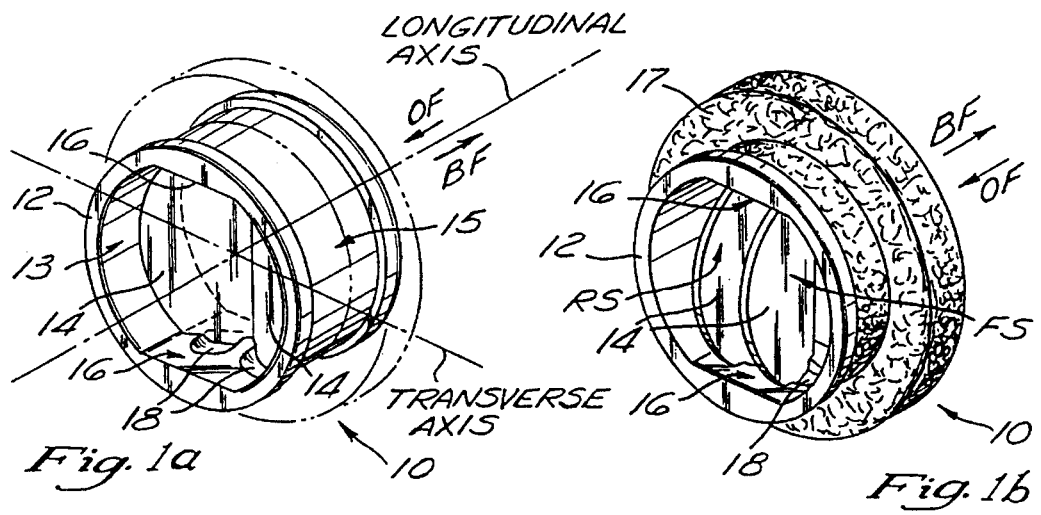
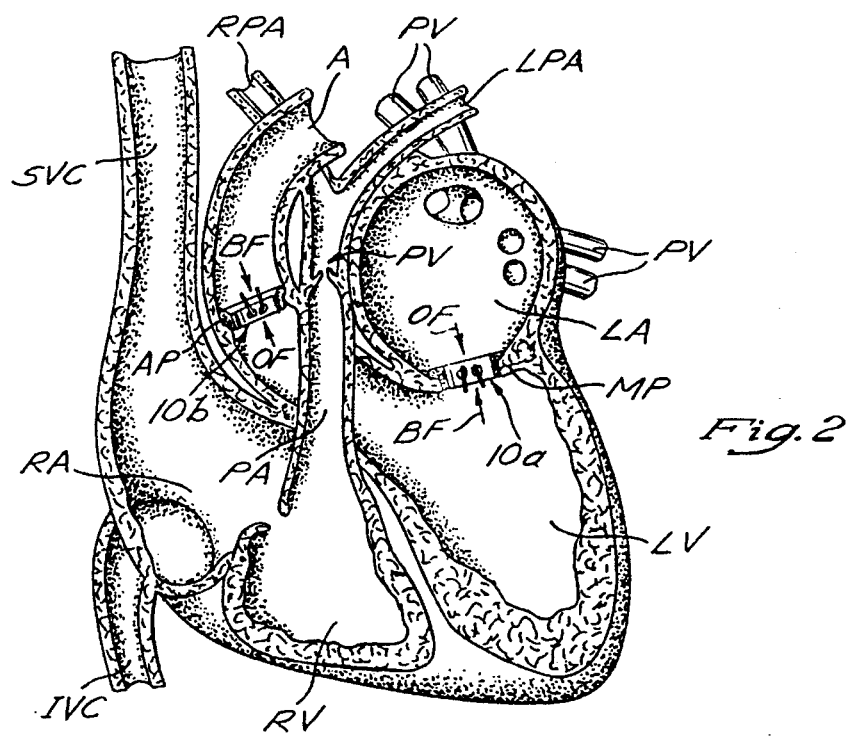
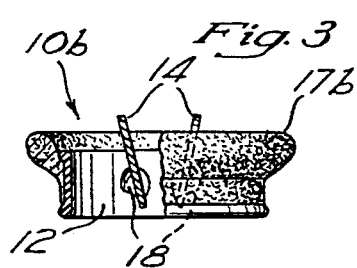
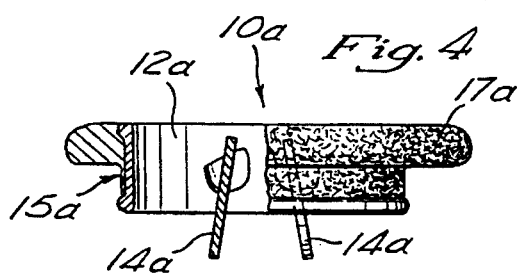

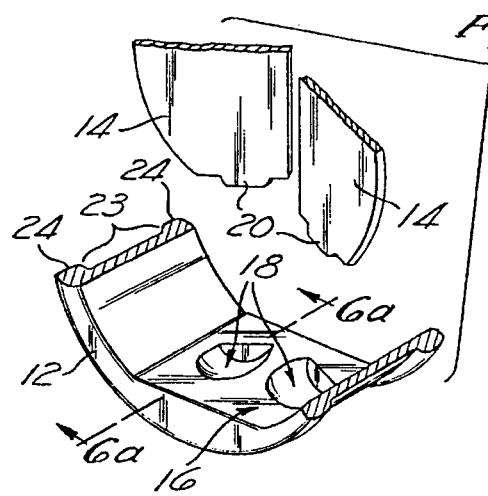
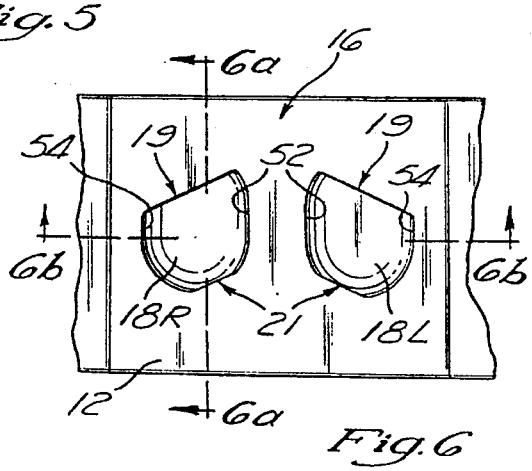
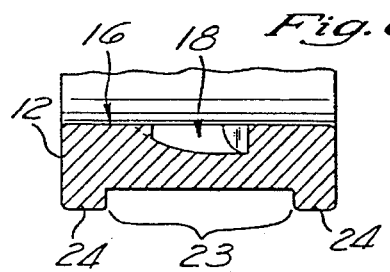
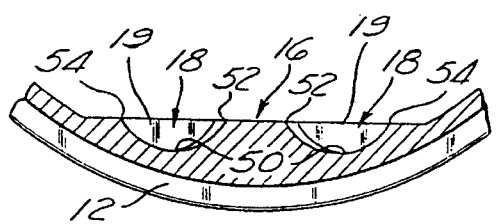
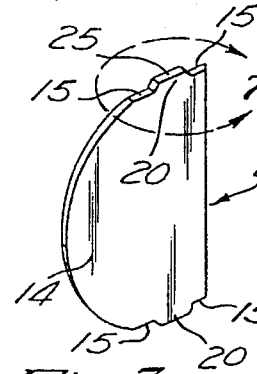
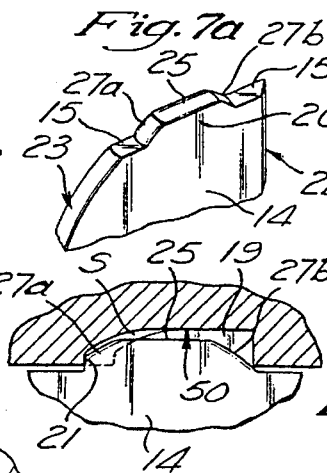
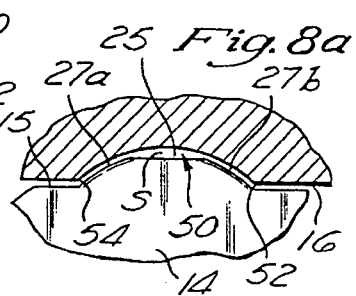
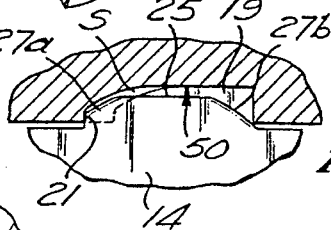
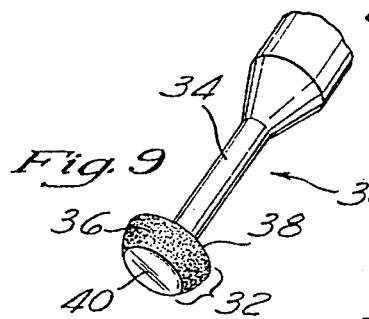
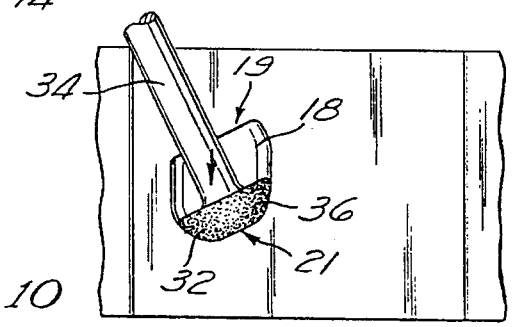

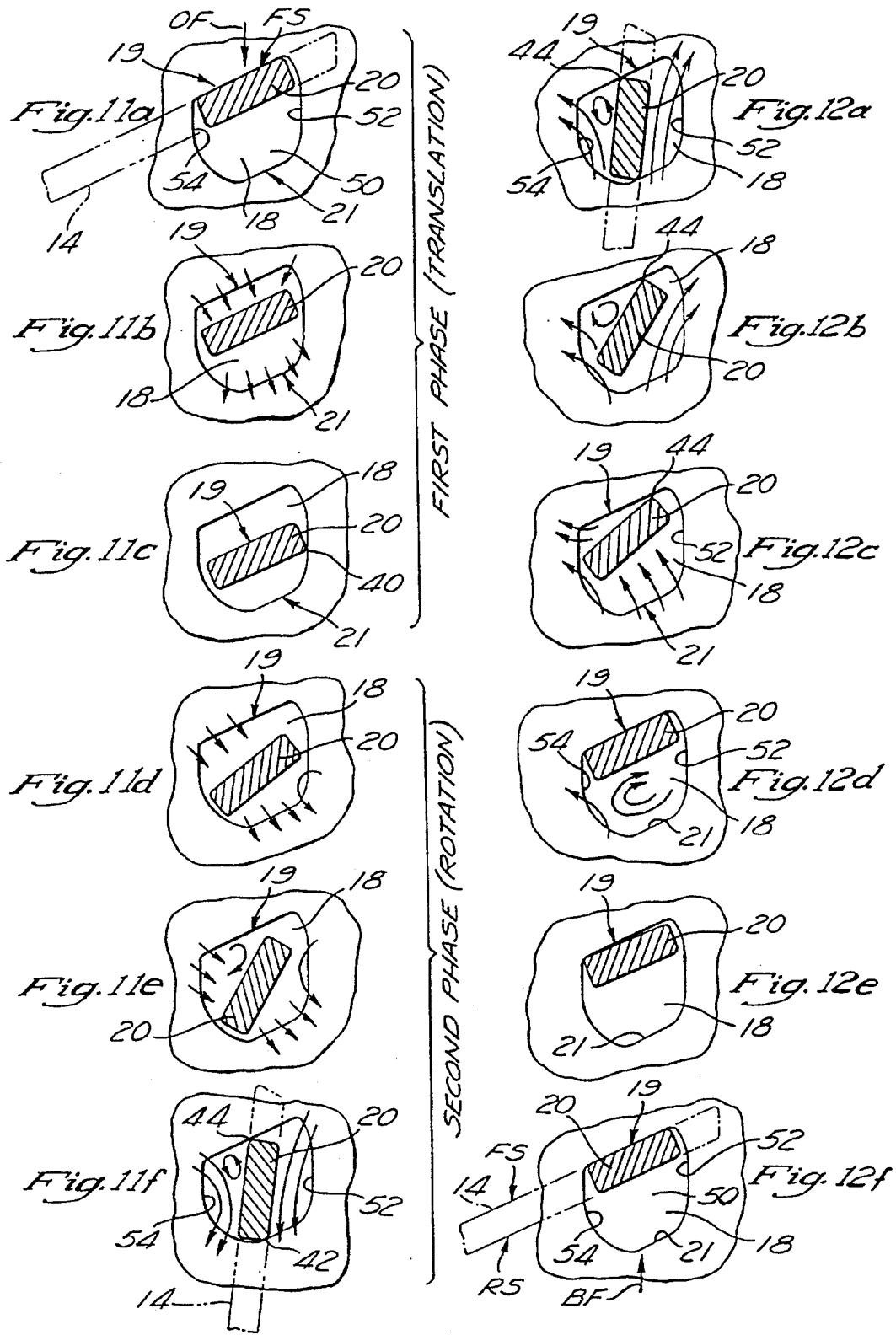

BILEAFLET MECHANICAL HEART VALVE HAVING CROPPED SLOT PIVOT CONFIGURATION AND METHOD FOR PREVENTING BLOOD STAGNATION THEREIN

FIELD OF THE INVENTION

The invention pertains generally to medical devices and, more particularly, to a prosthetic mechanical cardiovascular valve.

BACKGROUND OF THE INVENTION

Numerous types of prosthetic mechanical heart valves have previously been employed as replacements for malfunctioning endogenous anatomical heart valves.

In particular, one type of prosthetic mechanical heart valve is that known as a "bileaflet" mechanical valve. Mechanical valves of the bileaflet type typically comprise a pair of flat occluder leaflets pivotally mounted within a ring-like annular valve body. The leaflets will pivotally move, in response to hemodynamic movement of the blood, between an "open" position whereby blood is permitted to flow through the annular valve body in a first direction, and a "closed" position whereby blood is prevented from backflowing in a second direction opposite said first direction.

It is desirable for prosthetic heart valves of the bileaflet type to be constructed in a manner which will minimize or prevent the lodging or stagnation of blood within specific regions of the valve, as such stagnation or lodging of blood may result in thrombus formation and the occurrence of associated thromboembolic complications. In particular, one area where blood cells may tend to lodge or stagnate within the hinge or pivot mechanism the occluder leaflets are attached to the annular valve body. Accordingly, some valves of the prior art have incorporated modified pivot/hinge mechanisms purportedly capable of carrying out a self-clearing or self-"washing" function to remove any lodged or stagnating blood cells from the hinge or pivot mechanism.

Additionally, it is desirable for bileaflet mechanical prosthetic valves to be designed such that the leaflets will open and close softly, without slamming or unnecessary surface-to-surface contact, so as to minimize the likelihood of hemolysis (i.e., the breaking or rupture of blood cells).

Furthermore, it is desirable that heart valves of the bileaflet type be configured and constructed to withstand long term usage and wear, without fatigue, breakage or fracture of the valve components.

Examples of prosthetic mechanical heart valves of the prior art include those described in the following U.S. Pat. Nos.: 4,178,639 (Bokros), 4,272,854 (Bokros), 4,276,658 (Hanson, et al.), 4,328,592 (Klawitter), 4,363,142 (Meyer), 4,373,216 (Klawitter), 4,443,894 (Klawitter), 4,451,937 (Klawitter), 4,605,408 (Carpentier), 4,446,577 (Meyer, et al.), 4,676,789 (Sorensen, et al.), 4,692,165 (Bokros), 4,822,353 (Bokros), 4,863,458 (Bokros), 4,863,459 (Olin), 4,872,875 (Hwang), 4,888,010 (Bokros), 4,892,540 (Vallana), 4,923,465 (Knoch, et al.), 4,935,030 (Alonso), 4,995,881 (Knoch, et al.), 5,002,567 (Bona, et al.), 5,061,278 (Bicer), 5,078,738 (Couetil), 5,108,425 (Hwang), 5,116,366 (Hwang), 5,116,367 (Hwang, et al.), 5,123,920 (Bokros), 5,137,532 (Bokros, et al), 5,147,390 (Campbell), 5,152,785 (Bokros, et al.), 5,171,263 (Boyer, et al.), 5,178,632 (Hanson), 5,192,309 (Stupka, et al.), 5,192,313 (Budd, et al.), 5,197,980 (Gorshkov, et al.), as well as the following foreign patents and foreign patent publications: EP238181A, WO 86/05383, WO 91/11973, 0091746, 0465383A1, 0541215A1, WO 92/21305, 0023797, GB2055,452A, 0050439, GB2018396A, 0515324A1, WO92/02197, 0327790, EP289494, EP133608A, WO93/01767, EP89104A, EP256047A, EP436420A, EP 403649A, WO90/04367, EP176237A, and WO91/05524.

Although the prior art has included numerous surgically implantable bileaflet mechanical heart valves, there remains a need in the art for new or improved bileaflet mechanical valves capable of long term, cardiac functioning with minimal likelihood of thromboembolic complications or other untoward side effects.

SUMMARY OF THE INVENTION

The present invention is a bileaflet mechanical cardiovascular valve comprising an annular valve body having a central bore or blood flow passageway extending therethrough, and pair of occluder leaflets mounted therein. The occluder leaflets pivot back and forth between an open position whereby blood is permitted to outflow through the blood passageway, and a closed position whereby blood is prevented from backflowing through the blood passageway. The occluder leaflets have ear members or projections which are inserted into corresponding pairs of pivot slots formed at opposite locations on the inner surface of the annular valve body. Each pivot slot comprises a radially curved indentation or floor having a first flat end wall at one end thereof and a second flat end wall at an opposite end thereof. The first and second flat end walls of the pivot slots are preferably parallel to one another and are disposed at angles relative to the transverse axis of the annular valve body. The ear members of the occluder leaflets are snap fit into the pivot slots, and the ear members articulate or move within their respective pivot slots in a manner which facilitates pivotal opening and closing of the occluder leaflets. The occluder leaflets are preferably sized, relative to the annular valve body, such that a small amount of vertical or axial play exists, thereby allowing the occluder leaflets to float or move axially during operation. Such floating or axial movement of the occluder leaflets serves to prevent continuous surface-to-surface contact between the ear members and their respective pivot slots. Additionally, the ear members preferably have substantially flat end surfaces such that, even when an ear member becomes fully bottomed out in its respective pivot slot, a blood flow space will remain between the flat end surface of that ear member and the adjacent radiused floor of its respective pivot slot. The provision of such blood flow space permits some blow by or passage of blood, thereby preventing blood from stagnating within the confines of the pivot slots.

Further in accordance with the invention, the ear members are specifically shaped and configured, relative to their respective pivot slots such that, when the occluder leaflets move from their "closed" positions to their "open" positions, the ear members will initially undergo linear non-rotational movement within their respective pivot slots, followed by subsequent rotational movement therewithin. Such two-staged (i.e., non-rotational/rotational) movement further accomplishes a wiping action within the pivot slot, thereby further preventing blood from stagnating within the respective pivot slot.

Still further in accordance with the invention, the valve components are preferably formed of hard, nonporous materials such as titanium, and/or may be covered with pyrolytically deposited carbon coatings to provide a hard, smooth surface on the valve and to minimize the likelihood of antigenic or thrombogenic complications.

Further in accordance with the invention, there is provided a preferred truncated ball grinding tool, and a method of utilizing such tool to manufacture the preferred cardiovascular valve of the present invention.

Still further in accordance with the invention, the bileaflet mechanical valves of the foregoing character may be fitted with specifically configured suture rings and otherwise sized and adapted for surgical implantation at any suitable cardiac and/or non-cardiac site within the mammalian cardiovascular system, including implantation as a prosthetic replacement for the mitral and aortic valves of the human heart.

Further objects and advantages of the present invention will become apparent to those skilled in the art upon reading and understanding of the following detailed description, and the accompanying drawings.

BRIEF DESCRIPTION OF THE DRAWINGS

FIG. 1a is a perspective view of a bileaflet mechanical heart valve of the present invention having its leaflets disposed in their closed positions.

FIG. 1b is a perspective view of a bileaflet mechanical heart valve of the present invention having its leaflets disposed in their open positions.

FIG. 2 is a cross-sectional sketch of a human heart having bileaflet mechanical heart valves of the present invention implanted at both the aortic and mitral positions therein.

FIG. 3 is an enlarged, partially sectional, elevation view of a bileaflet mechanical heart valve of the present invention sized and outfitted for implantation in the aortic position.

FIG. 4 is an enlarged, partially sectional, elevation view of a bileaflet mechanical heart valve of the present invention sized and outfitted for implantation in the mitral position.

FIG. 5 is a partial perspective view of portions of a bileaflet mechanical heart valve of the present invention.

FIG. 6 is a plan view of a portion of the annular valve body of a bileaflet mechanical heart valve of the present invention.

FIG. 6a is a cross-sectional view through lines 6a–6a of FIG. 6.

FIG. 6b is a cross-sectional view through line 6b–6b of FIG. 6.

FIG. 7 is a perspective view of a leaflet component of a bileaflet mechanical heart of the present invention.

FIG. 7a is an enlarged perspective view of portion 7a of FIG. 7.

FIG. 8a is an elevational view of a portion of a bileaflet mechanical heart valve of the present invention showing the zone of articulation between a valve leaflet and the annular valve body when the leaflet is in its fully closed position.

FIG. 8b is an elevational view of a portion of a bileaflet mechanical heart valve of the present invention showing the zone of articulation between a valve leaflet and the annular valve body when the leaflet is in its fully open position.

FIG. 9 is a partial perspective view of a preferred truncated-ball grinding tool usable to manufacture a mechanical heart valve of the present invention.

FIG. 10a is a top view of the truncated ball grinding tool of FIG. 9 being utilized to form a cropped hinge slot in the annular valve body of a bileaflet mechanical valve of the present invention.

FIGS. 11a–11f are step-wise enlarged cross-sectional views showing the manner in which one of the occluder leaflets of a mechanical heart valve of the present invention moves from its closed position to its open position.

FIGS. 12a–12f are step-wise enlarged cross-sectional views showing the manner in which one of the occluder leaflets of a mechanical heart valve of the present invention moves from its open position to its closed position.

DETAILED DESCRIPTION OF A PREFERRED EMBODIMENT

The following detailed description, set forth in connection with the appended drawings, is intended only as a description of the presently preferred embodiments of the invention, and is not intended to represent the only embodiments in which the present invention may be constructed or utilized. Indeed, the present invention, or equivalents thereof, may be accomplished by different embodiments that are also intended to be encompassed within the spirit and scope of the invention.

As shown in the drawings, a presently preferred embodiment of a mechanical heart valve 10 of the present invention generally comprises an annular valve body 12 having a pair of occluder leaflets 14 pivotally mounted therein.

The annular valve body 12 has an inner surface 13 and an outer surface 15. The inner surface 13 defines a central bore or blood flow passageway which extends longitudinally through the valve body 12. The inner surface 13 includes upper and lower flat regions 16, formed at directly opposite locations. Right and left cropped pivot slots 18 are formed in each of the upper and lower flat regions 16, at directly opposite locations, to facilitate pivotal mounting of the occluder leaflets 14 within the annular valve body 12.

In the preferred embodiment shown, each pivot slot 18 comprises a generally radiused or curved floor 50 having a first cropped end formed by a first straight end wall 19 and a second cropped end formed by a second straight end wall 21. Straight end walls 19 and 21 are substantially parallel to one another. A curved inner edge 52 defines the inner or medial boundary of the radiused floor 50, such curved inner edge 52 extending from a first end of the first flat end wall 19 to a first end of the second flat end wall 21. Similarly, a curved outer edge 54 defines the outer or lateral boundary of the radiused floor 50, such curved outer edge extending from a second end of the first flat end wall 19 to a second end of the second flat end wall 21. Although the sizing and depth of the pivot slots may vary depending on the size of the recipient and the intended application of the valve, it is expected that a typical adult-sized cardiac valve would incorporate first flat end walls 19 having depths $D_1$ of approximately 0.6 mm from the flat surface 16 of the annular valve body 12 to the deepest point of the radiused floor 50 adjacent the first flat end wall 19. Similarly, the second flat end wall 21 of such adult cardiac valve would have a depth $D_2$ of approximately 0.2 mm. These end wall depths $D_1$, $D_2$ being the distance from the flat surface 16 to the deepest point of the radiused floor 50 adjacent the second flat end wall 21. In this regard, as can be seen in FIG. 6a, the pivot slots 18 are deeper at the end adjacent the first flat end wall 19 than at the opposite end adjacent the second flat end wall 21. Such end to end variation in the depth of the pivot slots facilitates a specifically designed opening and closing movement of the occluder leaflets 14, as described more fully herebelow and shown in detail in FIGS. 11 and 12.

Ear members 20 are projections which extend from opposite ends of the occluder leaflets 14. The ear members 20 are sized and configured to snap-fit into the corresponding right and left cropped pivot slots 18 formed in the upper and lower flat surfaces 16, as shown. Such snap fitting of the ear members 20 into the corresponding cropped pivot slots 18 serves to pivotally mount the occluder leaflets 14 beside one another within the central bore or blood flow passageway of the annular valve body 12.

In the preferred embodiment, each occluder leaflet 14 comprises a substantially flat, planar leaflet body of substantially uniform thickness T. Each leaflet 14 has a substantially flat front surface FS, a substantially flat rear surface RS, an arched outer edge 23, a straight beveled inner edge 22 and two straight flat end surfaces 15. In the preferred embodiment shown, a single ear member 20 extends from each straight flat end surface 15 on each end of the occluder leaflet 14. The ear members 20 may be integral of and continuous with the material of the leaflet body, thereby being of the same thickness T as the reminder of the leaflet body. The outer end of each ear member 20 forms a straight, substantially flat, ear member end surface 25 having spheroidal transitional regions 27a, 27d at either end thereof. The transitional regions 27 extend from the opposite ends of the flat surface 25 on the end of the ear member 20 to the underlying straight flat end surfaces 15 of the leaflet body. The front FS and rear RS surfaces of each ear member 20 are continuations of the flat front surface FS and rear surface RS of the occluder leaflet body from which that ear member 20 extends.

The ear members 20 are specifically sized and configured to fit within their respective pivot slots 18 in a manner which facilitates continuous or repetitious clearing or pumping of blood out of the interiors of the pivot slots, thereby minimizing the likelihood of blood stagnation and clot formation. The distance between the straight flat end surface 15 of each ear member 20, relative to the distance between the opposing flat surfaces 16 of the valve body 12, determines the amount of "float" or up and down movement which the occluder leaflets 14 may undergo. In this regard, the leaflets 14 may float or move up and down between the points where the straight flat end surfaces 15 on the opposite ends of the occluder leaflets 14 abut against the adjacent flat surfaces 16 of the annular valve body 12. In adult sized valves in the preferred embodiment, there is a difference of approximately 0.7 mm between a) the distance between the straight flat end surfaces 15 of the ear member 20 and b) the corresponding distance between flat surfaces 16 of the annular valve body 12. Thus, in the preferred embodiment, the members 20 are permitted to float or move up and down by a distance of approximately 0.7 mm between points at which the flat end surfaces 15 of the occluder leaflets 14 abut or bottom out against the adjacent flat surfaces 16 of the annular valve body 12. The ear members 20 are further sized and configured such that, when the flat end surface 15 of an occluder leaflet 14 is bottomed out against its adjacent flat surface 16 of the annular valve body 12, the spheroidal transitional surfaces 27 of the ear member may come into contact with adjacent surface of the pivot slot 18, but the flat end surface 25 of the ear member 20 does not fully contact the radiused floor 50 of the pivot slot 18. In this regard, a blood flow passage space S will always exist between the flat ear member end surface 25 and the adjacent radiused floor 50 of the pivot slot 18. The provision of such blood flow space S permits constant pumping or washing of blood between the flat ear member end surface 25 and the adjacent floor 50 of the pivot slot 18, thereby minimizing the likelihood that blood will stagnate within the pivot slot 15. Additionally, the potential for some float or up and down movement of the occluder leaflets 14 during operation prevents the occluder leaflets 14 from constantly rubbing against the surfaces of the pivot slots 18, thereby further minimizing the potential for hemolysis, or the initiation of untoward thrombogenesis.

Additionally, the relative configurations of the surfaces of the ear members 20, and their corresponding cropped pivot slots 18, serves to control the manner in which the occluder leaflets 14 move back and forth between their "closed" positions (FIGS. 1a, 8a, 11a and 12f) and their "open" positions (FIGS. 1b, 8b, 11f and 12a). These aspects of the invention are more fully described herebelow in the section of this description entitled "Operation and Functional Movement of the Valve Components".

When the occluder leaflets 14 are in their closed positions (FIGS. 1a, 8a, 11a and 12f), the straight beveled inner edges 22 of the leaflets 14 are in abutment with one another while the arched outer edges 23 of the leaflets abut against the arched or annular inner surface 13 of the annular valve body 12. Thus, when so positioned, the occluder leaflets 14 will substantially block blood flow in the second or backflow direction BF through the bore or blood flow passageway of the annular valve body 12.

When the occluder leaflets 14 are in their open positions, as shown in FIG. 1b, the rear surfaces RS of the leaflets 14 are disposed in opposing, substantially parallel, spaced-apart relation to one another, as shown, such that blood is permitted to flow, in the first direction or outflow direction OF, through the central bore or blood flow passageway of the annular valve body 12.

A suture ring 17, formed of suture-needle penetrable material such as woven dacron, is mounted about the outer surface 15 of the annular valve body 12 to facilitate suturing of the prosthetic valve 10 in its desired anatomical position.

Two (2) typical anatomical positions (mitral and aortic) wherein the prosthetic valve 10 of the present invention is surgically implanted are shown in FIG. 2. The anatomical structures of the human heart and major blood vessels are labeled on FIG. 2 in accordance with the following legend:

| | |
|---|---|
| PV | Pulmonary Veins |
| PA | Pulmonary Artery |
| RPA | Right Pulmonary Artery |
| LPA | Left Pulmonary Artery |
| SVC | Superior Vena Cava |
| IVC | Inferior Vena Cava |
| A | Aorta |
| RA | Right Atrium |
| RV | Right Ventricle |
| LA | Left Atrium |
| LV | Left Ventricle |
| AP | Aortic Valve Position |
| MP | Mitral Valve Position | i. Mitral valve Embodiment

With reference to FIG. 2, a first embodiment of the valve 10a is implanted in the mitral position MP and a second embodiment of the valve 10b is implanted at the aortic position AP.

The prosthetic valve 10a implanted at the mitral position MP is shown in partial cross-sectional view in FIG. 4. The structural components of mitral embodiment of the valve 10a are typically be sized as follows:

An Example of Sizing of Pediatric Mitral Valve 25 m Could Be

Annular Body OD=0.952 Inches

Annular Body ID=0.854 Inches

Leaflet Thickness=0.035 Inches

Suture Ring OD=1.03 Inches

An Example of Sizing of Adult Mitral Valve 29 m Could Be

Annular Body OD=1.102 Inches

Annular Body ID=1.00 Inches

Leaflet Thickness=0.035 Inches

Suture Ring OD=1.19 Inches

Also, in the mitral embodiment of the valve 10a, as shown in FIGS. 2 and 4, the dacron suture ring 17a is specifically sized and configured, as shown, to seat within the annular opening created between the left atrium LA and left ventricle LV when the diseased or malfunctioning endogenous mitral valve is surgically incised and removed.

ii. Aortic Valve Embodiment

The aortic prosthetic valve 10b of the present invention, as shown in FIGS. 2 and 3, is typically sized as follows:

An Example Of Sizing of Pediatric Aortic Valve 19A Could Be

Annular Body OD=0.739 Inches

Annular Body ID=0.657 Inches

Leaflet Thickness=0.024 Inches

Suture Ring OD=0.79 Inches

An Example of Sizing of Adult Aortic Valve 27A Could Be

Annular Body OD=1.030 Inches

Annular Body ID=0.928 Inches

Leaflet Thickness=0.035 Inches

Suture Ring OD=1.11 Inches

Also, in the aortic embodiment of the valve 10b shown in FIGS. 2 and 3, the dacron suture ring 17b specifically sized and configured, as shown, to seat within the annular opening created by surgical excision and removal of the diseased or malfunctioning endogenous aortic valve.

iii. Preferred Configuration and Fabrication of the Valve Components

The presently preferred construction and method for manufacturing the prosthetic valve 10 of the present invention is shown in FIGS. 5–10.

The annular valve body 12 is initially machined from suitable material such as titanium, titanium alloys stainless steel, or pyrolytic carbon coated graphite, etc.

An annular groove or depression 23 is machined about the central region of the outer surface 15 of the annular valve body 12, thereby forming annular flanges 24 about the front and rear edges of the outer surface 15 of the annular valve body 12. Such annular groove or depression 23 receives and accommodates the suture ring 17, thereby facilitating mounting of the suture ring 17 on the valve 10.

The inner surface 13 of the annular valve body 12 has arched side walls traversing between the ends of the upper and lower flat regions 16, as shown. The upper and lower flat regions 16 of the inner surface 13 of the annular valve body 12 are specifically sized to accommodate the formation therein of opposing pairs of cropped pivot slots 18.

The radiused floor 50 of each cropped pivot slot 18 is formed by machining or other appropriate means. In the preferred embodiment, the cropped pivot slots 18 are formed by grinding into the flat regions 16 by the rotating machine tool 30 shown in FIGS. 9 and 10. The preferred rotating machine tool 30 comprises a truncated ball head 32 having a spherical lateral surface 36, a flat proximal surface 38 in a flat distal surface 40. The spherical lateral surface of the head 32 is textured so as to grind into the material of the annular valve body 12 upon rotation of the head 32 at sufficient velocity. Such rotating machine tool 30 is preferably utilized to machine the cropped pivot slot 18 by initially compressing the truncated ball head 32 of the tool 30 downwardly into the flat region 16 of the inner surface 13 of the annular valve body 12, and subsequently advancing the machine tool 30 in a forward direction (see arrow on FIG. 10) for a predetermined distance to a point where the flat distal surface 40 of the machine tool 30 forms the desired second flat end wall 21 of the pivot slot 18. Thereafter, the machine tool 30 is retracted in the opposite direction to a point where the flat proximal surface 38 of the machine tool 30 forms the desired first flat end wall 19 of the pivot slot 18. Thereafter, the machine tool 30 is again advanced in the forward direction to a point where the rotating truncated ball head 32 is rotated in the lid portion of the pivot slot 18, between the first and second vertical end wall 19, 21 thereof. When so positioned, the machine tool 30 is lifted away from the flat surface 16 of the valve body 12, thereby removing the rotating truncated ball head 32 from the pivot slot 18.

It will be appreciated that, in order to maintain consistent reproducible spacing between adjacent cropped pivot slots 18, two (2) of the rotary machine tools 30 may be joined in mechanically fixed or prepositioned relation to one another. The separate rotating heads 32 of the two (2) mechanically fixed or prepositioned machine tools 30 may then be simultaneously or concurrently rotated and guided into contact with the flat region 16 of the inner surface 13 of the annular valve body 12 to form the desired spaced-apart pair of cropped hinge slots 18, by a single machine process. This will make certain that the spacing and configuration of the individual crop hinged slots 18 is reproducible and consistent. Each occluder leaflet 14 may be cut from a flat sheet of appropriate material such as titanium, titanium alloy, stainless steel or pyrolytic carbon coated graphite, etc. Each occluder leaflet 14 has an angle-cut (i.e., beveled) inner or leading edge 22 and an arched outer or trailing 23. The ear members 20 located on opposite ends of the leaflets 14, are specifically configured to extend into, pivot within, and clear blood cells from, their corresponding cropped pivot slots 18.

The provision of the flat end surface 25 on each ear member 20 ensures that the desired blood flow space S will remain between such flat end surface 25 and the adjacent radially concaved floor 50 of the pivot slot 18 into which the ear member 20 is inserted. Such space or gap between the flat end surface 25 of an ear member 20 and the radially concaved floor 50 of the cropped pivot slot 18 is specifically shown in FIGS. 8a and 8b. The hemodynamic force of the flowing blood will force blood to flow through the space or gap between the flat end surface 25 of each ear member 20 and the adjacent radially concaved floor 50 of its cropped pivot slot 18, thereby facilitating "washing" or dislodgement of any blood cells, which may have become adherent to, or otherwise resident within, the cropped pivot slot 18.

After fabrication of the annular valve body 12 and occluder leaflets 14 have been completed, the components of the valve are preferably subjected to a pyrolytic carbon deposition process. By such pyrolytic deposition process, a dense coating of carbon is uniformly deposited over the entire surfaces of such components. Such dense carbon coating serves to minimize the thrombogenicity which could result from surface porosity or surface roughness of the valve components. The equipment and methodology utilized to effect such pyrolytic deposition process is well known in the art.

iv. Preferred Method of Assembling The Valve Components

After the annular valve body 12 and occluder leaflets 14 have been coated with pyrolytic carbon, they are then processed through various grinding & polishing operations before the finished parts are ready for assembly. The valve 10 is assembled by snap fitting a pair of occluder leaflets 14 into the annular valve body 12 and by mounting the desired dacron suture ring 17 on the outer surface 15 of the annular valve body 12.

When the ear members 20 are sized and configured in accordance with the above-described preferred embodiment, the ratio of ear member thickness T to pivot slot width is sufficiently great as to reduce the degree of precision required when assembling the occluder leaflet 14 into the annular valve body 12. Accordingly, each occluder leaflet 14 is mounted into the annular valve body 12 by first placing one ear member 20 into its pivot slot 18 before sliding the opposite ear member 20 into the opposite pivot slot 18. When performed in this manner, the amount of deflection required of the annular valve body 12 and/or leaflet 14 is less than the actual height of the opposite ear member 20, thereby minimizing the degree of deformation which will occur during snap fitting of the occluder leaflets 14 into the annular valve body 12.

v. Operation and Functional Movement of the Valve Components

The configurational aspects of the annular valve body 12 and occluder leaflets 14 as described herein, enable the valve 10 of the present invention to perform its desired hemodynamic valving function, while continuously dislodging or "washing" any lodged blood cells from the inner surfaces of the recessed cropped pivot slots 18.

The specific manner in which each ear member 20 travels within its corresponding cropped pivot slot 18, as the occluder leaflets repeatedly open and close, is illustrated in FIGS. 11 and 12.

A. Opening of the Occluder Leaflets

FIGS. 11a–11f provide a step-wise showing of the preferred two stage movement of an ear member 20 within a cropped pivot slot 18 as the occluder leaflet 14 moves from its fully closed position (FIG. 11a) to its fully open position (FIG. 11f). Such two stage movement is characterized by an initial translation of the ear member 20 in the first or outflow OF direction, followed by the subsequent rotation of the ear member 20 as the occluder leaflet 14 pivots to its fully open position.

As shown, when the occluder leaflet 14 is in its fully closed position, the front surface FS of the ear member 20 is in abutting contact with the first straight cropped surface 19 of the pivot slot 18 (FIG. 11a).

As the pressure pulse of blood begins to push against the front surface FS of the occluder leaflet 14 in the first or outflow of direction OF, the ear member 20 will initially translate straight forward in such first or outflow direction OF, within the pivot slot 18 (FIG. 11b).

As the ear member 20 translates forward within the pivot slot 18, a first corner 40 of the ear member 20 will contact the inner edge 52 of the pivot slot 18 (FIG. 11c).

The contact of the first corner 40 of the ear member 20 with the inner edge 52 of the pivot slot 18 creates a pivoting point such that the occluder leaflet 14 will begin to rotate inwardly such that the ear member 20 will undergo a corresponding rotational movement within the pivot slot 18 (FIG. 11d).

As the occluder leaflet 14 and ear member 20 proceed to pivot, the blood outflow impinging against the front surface FS of the occluder leaflet 14 will begin to flow past the occluder leaflet, thereby flowing through the annular bore or passageway of the valve 10 (FIG. 11e)

When the occluder leaflet 14 has undergone complete pivotal movement to its fully open position, a second corner 42 of the ear member 20 will contact the second flat cropped surface 21 of the pivot slot 18 while the contralateral third corner 44 of the ear member 20 will contact the first cropped surface 19 of the slot 18. Such simultaneous contact of the second and third corners 42, 44 of the ear member with the first and second cropped surfaces 19, 21 of the slot 18 will stop the rotational movement of the occluder leaflet 14, with the leaflet 14 in its fully open position (FIG. 11f).

B. Closing of the Occluder Leaflets

As the hemodynamic movement of the blood reverses direction (as occurs when the systolic contraction of the heart ends and the diastolic contraction of the heart begins) blood will tend to return in the backflow direction BF through the central bore or passageway of the valve 10 (FIG. 12a). Such reversal of the hemodynamic movement of the blood will exert backflow pressure against rear surface RS of the occluder leaflet 14, thereby inducing the occluder leaflet 14 to simultaneously undergo a) linear translation in the second or backflow direction BF and b) rotational movement toward its closed position. Upon such simultaneous translatory (linear) and rotational movement of the occluder leaflet 14, the ear 20 will undergo corresponding simultaneous translatory and pivotal movement within its corresponding pivot slot 18. As such movement occurs, the third corner 44 of the ear member 20 may slip medially across the first cropped surface 19 of the pivot slot 18 (FIG. 12b).

As the third corner 44 of ear 20 slips medially across the first cropped surface 19 of the slot 18, the occluder leaflet 14 will continue to travel toward its closed position, thereby beginning to block the backflow of blood in the backflow direction BF through the hollow bore or passageway of the valve 10 (FIG. 12c).

When the occluder leaflet 14 reaches its fully closed position, the straight front surface FS of the ear member 20 will once again come into abutting contact with the first straight cropped edge 19 of the slot 18 (FIG. 12d). At the same time, the beveled inner edges 22 of the two occluder leaflets 14 come into abutting contact with one another and the occluder leaflets 14 will thereby be supported at angles defined cooperatively by (a) the slant angle of the first flat cropped surfaces 19 of the pivot slots 18, and; (b) the bevel angel of the inner edges 22 of the occluder leaflets 14.

The ear member 20 may undergo a slight reactive bounce away from the cropped surface 19 of the slot 18 (FIG. 12e).

After any reactive "bounce" away from the cropped surface 19 of the slot 18, the front surface FS of the ear member 20 will return to a firmly seated position in abutment with the first straight cropped surface 19 of the pivot slot 18 as the occluder leaflet 14 rests in its fully closed position (FIG. 12f), thereby blocking bloodflow in the backflow BF direction.

As the hemodynamic movement of the blood again reverses to the outflow direction OF, the occluder leaflet 14 and ear 20 will again transition from the fully closed to the fully open position, as illustrated in FIGS. 11a–11f.

It is to be appreciated that, in normal operation, the closing of the leaflets 14 may not always occur in perfect simultaneity. In recognition of this fact, the leaflets 14 are specifically designed and configured to facilitate slightly non-simultaneous closing of the leaflets 14 with minimal shock or stress exerted on the leaflets and other components of the valve 10. Specifically, when one leaflet 14 reaches its fully closed position (FIG. 11a or 12f) before the other, the force of the flowing blood against the rear surface RS of the angularly disposed leaflet 14 will cause the leaflet 14 to bias or move inwardly such that the ear member 20 will slide inwardly along flat end wall 19 of the slot 18, adjacent the curved inner surface 52 thereof. Thereafter, as the opposite leaflet reaches its fully closed position, the angularly tapered inner edges 22 of the leaflets 14 will collide with one another, and will seat against one another, thereby forcing the first-closing leaflet 14 back in the direction of the curvilinear outer edge 54 of its slot 18 with the ear 20 sliding back along flat end wall 19 of pivot slot 18, toward adjacent outer curved edge 54. This will cause the first closing leaflet to react by moving back toward the middle of the slot, and such movement will be transmitted to the opposite leaflet 14 by abutment of the inner edges 22 of the leaflets 14. This results in a momentary back and forth jostling motion of the two leaflets 14 until equilibrium has been attained, with both leaflets 14 is stabilized closed positions. This momentary jostling motion of the leaflets 14 acts as a shock absorbing feature which a) reduces high initial closing forces and b) creates a more gentle closure when such closure occurs without perfect simultaneity.

The above-described opening and closing movements of each ear member 20 within its corresponding cropped pivot slot 18 creates a combination of (a) a pumping action as the ear member 20 translates from its fully closed position (FIG. 11a) to its forward-most translated position (FIG. 11c), and (b) a rotational wiping or flushing action as the ear member 20 rotates to its open position (FIGS. 11b–11f) and again back to its closed position (FIGS. 12a–12f).

During the translational phase of the occluder leaflet 14 opening (FIGS. 11a–11f), the blood flow will exert greater pressure on the front surface FS of the leaflet 14, then on the rear surface RS thereof. During such translational phase of the movement of the occluder leaflet 14, blood will briskly flow through the space or gap which exists between the flat end surface 25 of each ear member 20 and the adjacent radiused floor of its cropped pivot slot 18. The brisk passage of blood through such confined space or gap will effect the pumping washing action within the recessed pivot slot 18 to reduce the likelihood of blood stagnation within such pivot slot 18.

During the subsequent rotational phase of the opening movement (FIGS. 11b–11f) of the occluder leaflet 14, the first and second semi-spheroidal transitional surfaces 27a, 27b of the ear member 20 will pass over or ride against the adjacent radially concaved floor 50 of the pivot slot 18, thereby furthering the dislodgement of any stagnating blood within the pivot slot 18.

Upon closing of the occluder leaflet 14 (FIGS. 12a–12f) the simultaneous rotational and translational movement of the ear member 20 within the slot 18 will once again result in the channeling or "pumping" of blood flow through the space between the flat end surface 25 of the ear member 20 and the radially concaved floor 50 of the slot 18, and rotational wiping or flushing by action of the semi-spheroidal transitional surfaces 27a, 27b of the ear member 20 against the adjacent concaved floor 50 of the slot 18.

As the valve 10 undergoes constant repetitions of the above-described opening and closing movements, the translation and rotation of each ear member 20 within each pivot slot 18 will perform a self clearing or "washing" function thereby reducing the likelihood of blood stagnation within the recessed pivot slot 18 and resultant thromboembolic consequences.

Although the invention has been described herein with specific reference to presently .preferred embodiments thereof, it will be appreciated by those skilled in the art that various additions, modifications, deletions and alterations may be made to such preferred embodiments without departing from the spirit and scope of the invention. Accordingly, it is intended that all reasonably foreseeable additions, deletions, alterations and modifications be included within the scope of the invention as defined in the following claims.

What is claimed is:

1. A bileaflet mechanical cardiovascular valve comprising:
   a) an annular valve body having an inner surface and a central blood flow passageway extending therethrough, said valve body having an blood inflow side and a blood outflow side;
   b) first and second pairs of pivot slots formed on opposite sides of the inner surface of the annular valve body, a central axis defined between each pair of pivot slots, each pivot slot comprising:
      i) an indentation formed in said valve body and having a curved configuration;
      ii) a first flat end wall at one end of said indentation adjacent said blood inflow side, said first flat end wall having first and second ends;
      iii) a second flat end wall at an end of said indentation opposite said first flat end wall and adjacent said blood outflow side, said second flat end wall having first and second ends, said second flat end wall being substantially parallel to said first flat end wall, and said first and second flat end walls disposed at an angle transecting the central axis of said valve body;
      iv) an inner curved edge adjacent the central axis extending from the first end of the first flat end wall to the first end of the second flat end wall, said inner curved edge comprising a curved upper portion, a substantially straight central portion, and a curved lower portion; and,
      v) an outer curved lateral edge extending from the second end of the first flat end wall to the second end of the second flat end wall, said outer curved lateral edge comprising a substantially straight upper portion and a curved lower portion;
   c) right and left occluder leaflets having first and second ends, and ear members extending from the first and second ends thereof, said ear members being disposed within said pivot slots to pivotally mount said occluder leaflets within said annular valve body;
   d) said occluder leaflets being thereby pivotally movable between:

i) an open position wherein said occluder leaflets are positioned to allow blood to flow in a first direction through said blood flow passageway; and ii) a closed position wherein said occluder leaflets prevent blood from backflowing through said blood flow passageway in a second direction, opposite said first direction.

2. The valve of claim 1 wherein an ear member extends from each end of each occluder leaflet, each said ear member comprising a rigid projection having a substantially flat end surface with generally spheroidal transition surfaces formed at opposite ends of said substantially flat end surface.

3. The valve of claim of 1 wherein the inner edges of the occluder leaflets are beveled and wherein the angle at which said inner edges are beveled corresponds to the angle at which said first flat end walls of said pivot slots are disposed relative to the transverse axis of the valve body, such that when said occluder leaflets are in their closed positions, the beveled inner edges of the occluder leaflets will abut against one another and the ear members will rest against the first flat end walls of the pivot slots.

4. The valve of claim 1 wherein said ear members are sized relative to said pivot slots such that, when pressure is exerted in said first direction against a first side of said occluder leaflets while said leaflets are in their closed positions, said ear members will initially undergo axial movement in said first direction and thereafter, said ear members will rotate within said pivot slots until said occluder leaflets have reached their open positions.

5. The valve of claim 4 wherein the ear members have a plurality of corners and are sized relative to said pivot slots such that, as said ear members undergo said initial axial movement in said first direction, a first corner of each ear member will come into abutment with an edge of the pivot slot, thereby establishing a pivot-point about which said ear member subsequently rotates.

6. The valve of claim 5 wherein said ear members are further configured such that, as said ear members rotate second and third corners of said ear members will subsequently come into contact with the opposite first and second flat end walls of the pivot slot, thereby stopping the rotation of said ear member and the corresponding rotation of the occluder leaflet from which that ear member extends.

7. The valve of claim 6 wherein the ear members and pivot slots are configured such that said second and third corners of said ear member will simultaneously come into abutment with the first and second flat end walls.

8. The valve of claim 3 wherein the occluder leaflets are sized, relative to the annular valve body, such that the occluder leaflets may undergo some axial movement in opposite directions between points whereat each ear member is bottomed out in its respective pivot slot.

9. The valve of claim 8 wherein the space between said flat end surface of said ear member and the adjacent radial floor of the pivot slot is approximately 0.090–0.150 inches in length, when said ear member is bottomed out in said pivot slot.

10. The valve of claim 1 wherein each of said ear member is configured with a substantially flat end surface and first and second spheroidal transition surfaces at either end of said substantially flat end surface and wherein said occluder leaflets are sized such that, when said ear members are pivotally inserted into said pivot slots, a blood-passage space will remain between the substantially flat end surface of each ear member and the spheroidal surface of the pivot slot within which said ear member is disposed.

11. The valve of claim 1 wherein each ear member is sized and configured relative to the pivot slot within which it resides, such that, as the occluder leaflet moves from its closed position to its open position, said ear member will undergo:

a first axial phase of movement whereby said ear member axially translates within said pivot slot in the longitudinal direction of blood outflow through the annular valve body; followed by, a second rotational phase of movement whereby said ear member undergoes pivotal rotation within said pivot slot as the occluder leaflet returns to its open position.

12. The valve of claim 11 wherein each ear member is further sized and configured such that, as said occluder leaflet return from their open position to its closed position, said ear member will undergo simultaneous rotation and translation to its fully closed position.

13. The valve of claim 1 wherein said occluder leaflets are sized and configured relative to said pivot slots such that, when said occluder leaflets are in their closed positions, said ear members will be in abutment with the first flat end wall of each pivot slot.

14. The valve of claim 11 wherein the first axial phase movement of each ear member within each pivot slot continues until a first corner of said ear member comes into contact with a point on said pivot slot, thereby forming a pivot-point about which said second rotational phase of movement begins.

15. The valve of claim 14 wherein said second rotational phase of movement continues until at least one corner of said ear member comes into contact with at least one flat end wall of said pivot slot, thereby stopping said second rotational phase of movement with said leaflet in its fully open position.

16. The valve of claim 15 wherein said second rotational phase of movement continues until a second corner of said ear member abuts against said first flat end wall of said pivot slot and a third corner of said ear member abuts against said second flat end wall of said pivot slot, thereby stopping said rotational movement with said leaflet in its fully open position.

17. The valve of claim 16 wherein said second corner of said ear member slips medially along said first flat end wall of said pivot slot as said leaflet undergoes pivotal rotation from its open position to its closed position.

18. A bileaflet mechanical cardiovascular valve comprising:

a) an annular valve body having an inner surface and a central blood flow passageway extending therethrough;

b) first and second pairs of pivot slots formed on opposite sides of the inner surface of the annular valve body, each pivot slot comprising:

i) an indentation formed in said valve body and having a curved configuration;

ii) a first flat end wall at one end of said indentation, said first flat end wall having first and second ends;

iii) a second flat end wall at an end of said indentation opposite said first flat end wall, said second flat end wall having first and second ends, said second flat end wall being substantially parallel to said first flat end wall;

iv) an inner curved edge extending from the first end of the first flat end wall to the first end of the second flat end wall; and, v) an outer curved lateral edge extending from the second end of the first flat end wall to the second end of the second flat end wall;

c) right and left occluder leaflets having first and second ends, and ear members extending from the first and second ends thereof, said ear members being disposed within said pivot slots to pivotally mount said occluder leaflets within said annular valve body;

d) said occluder leaflets being thereby pivotally movable between:
   i) an open position wherein said occluder leaflets are positioned to allow blood to flow in a first direction through said blood flow passageway; and
   ii) a closed position wherein said occluder leaflets prevent blood from backflowing through said blood flow passageway in a second direction, opposite said first direction;

e) wherein said ear members are sized relative to said pivot slots such that, when pressure is exerted in said first direction against a first side of said occluder leaflets while said leaflets are in their closed positions, said ear members will initially undergo axial movement in said first direction and thereafter, said ear members will rotate within said pivot slots until said occluder leaflets have reached their open positions;

f) wherein the ear members have a plurality of corners and are sized relative to said pivot slots such that, as said ear members undergo said initial axial movement in said first direction, a first corner of each ear member will come into abutment with an edge of the pivot slot, thereby establishing a pivot-point about which said ear member subsequently rotates, and g) wherein said ear members are further configured such that, as said ear members rotate, second and third corners of said ear members will subsequently come into contact with the opposite first and second flat end walls of the pivot slot, thereby stopping the rotation of said ear member and the corresponding rotation of the occluder leaflet from which that ear member extends.

19. The valve of claim 10 wherein the ear members and pivot slots are configured such that said second and third corners of said ear member will simultaneously come into abutment with the first and second flat end walls.

20. A prosthetic mechanical cardiovascular valve, comprising:
   a) an annular valve body with right and left occluder leaflets pivotally mounted therein;
   b) opposing pairs of right and left cropped pivot slots formed at opposite locations on the inner surface of said annular valve body, each said cropped pivot slot comprising:
      i) an indentation formed in said valve body and having a curved configuration;
      ii) a first flat end wall at one end of said indentation, said first flat end wall having first and second ends;
      iii) a second flat end wall at an end of said indentation opposite said first flat end wall, said second flat end wall having first and second ends, said second flat end wall being substantially parallel to said first flat end wall;
      iv) an inner curved edge extending from the first end of the first flat end wall to the first end of the second flat end wall; and,
      v) an outer curved lateral edge extending from the second end of the first flat end wall to the second end of the second flat end wall;
   c) ear members extending from said occluder leaflets into said cropped pivot slots to pivotally mount said occluder leaflets within said annular valve body, said ear members being sized and configured relative to said cropped pivot slots to facilitate opening and closing of said occluder leaflets in response to changes in hemodynamic movement of blood through said annular valve body;
   d) wherein each ear member is sized and configured relative to the pivot slot within which it resides, such that, as the occluder leaflet moves from its closed position to its open position, said ear member will undergo:
      i) a first axial phase of movement whereby said ear member axially translates within said pivot slot in the longitudinal direction of blood outflow through the annular valve body; followed by,
      ii) a second rotational phase of movement whereby said ear member undergoes pivotal rotation within said pivot slot as the occluder leaflet returns to its open position;
   e) wherein the first axial phase movement of each ear member within each pivot slot continues until a first corner of said ear member comes into contact with a point on said pivot slot, thereby forming a pivot-point about which said second rotational phase of movement begins;
   f) wherein said second rotational phase of movement continues until at least one corner of said ear member comes into contact with at least one flat end wall of said pivot slot, thereby stopping said second rotational phase of movement with said leaflet in its fully open position; and
   g) wherein said second rotational phase of movement continues until a second corner of said ear member abuts against said first flat end wall of said pivot slot and a third corner of said ear member abuts against said second flat end wall of said pivot slot, thereby stopping said rotational movement with said leaflet in its fully open position.

21. The valve of claim 20 wherein said second corner of said ear member slips medially along said first flat end wall of said pivot slot as said leaflet undergoes pivotal rotation from its open position to its closed position.

22. A prosthetic mechanical cardiovascular valve, comprising:
   a) an annular valve body having right and left occluder leaflets pivotally mounted therein, and an inner surface;
   b) opposing pairs of right and left pivot slots formed at opposite locations on the inner surface of said annular valve body;
   c) ear members extending from said occluder leaflets into said pivot slots to pivotally mount said occluder leaflets within said annular valve body, said ear members being sized and configured relative to said pivot slots to facilitate opening and closing of said occluder leaflets in response to changes in hemodynamic movement of blood through said annular valve body;
   d) said occluder leaflets being thereby pivotally movable between:
      i) an open position wherein said occluder leaflets are positioned to allow blood to flow in a first direction through said blood flow passageway; and
      ii) a closed position wherein said occluder leaflets prevent blood from backflowing through said blood flow passageway in a second direction, opposite said first direction;
   e) wherein each ear member is sized and configured relative to the pivot slot within which it resides, such that, as said occluder leaflets move from their closed position to their open position, said ear member will undergo:

i) a first axial phase of movement whereby said ear member axially translates within said pivot slot in the longitudinal direction of blood outflow through the annular valve body; followed by,
  ii) a second rotational phase of movement whereby said ear member undergoes pivotal rotation within said pivot slot as said occluder leaflets return to their open position; and
f) wherein each ear member is further sized and configured such that, as said occluder leaflets return from their open position to their closed position, said ear member will undergo simultaneous rotation and translation to its fully closed position.

23. The valve of claim 22, wherein the first axial phase movement of each ear member within each pivot slot continues until a first corner of said ear member comes into contact with a point on said pivot slot, thereby forming a pivot-point about which said second rotational phase of movement begins.

24. The valve of claim 23, wherein each pivot slot comprises at least one flat end wall, and wherein said second rotational phase of movement continues until at least one corner of said ear member comes into contact with at least one flat end wall of said pivot slot, thereby stopping said second rotational phase of movement with said leaflet in its fully open position.

25. The valve of claim 24 wherein said second rotational phase of movement continues until a second corner of said ear member abuts against said at least one flat end wall of said pivot slot and a third corner of said ear member abuts against another flat end wall of said pivot slot, thereby stopping said rotational movement with said leaflet in its fully open position.

26. The valve of claim 24 wherein said second corner of said ear member slips medially along said at least one first flat end wall of said pivot slot as said leaflet undergoes pivotal rotation from its open position to its closed position.

* * * * *